US009315477B2

(12) United States Patent
Marder et al.

(10) Patent No.: US 9,315,477 B2
(45) Date of Patent: Apr. 19, 2016

(54) MATERIALS HAVING ELECTRON DEFICIENT MOIETIES AND METHODS OF SYNTHESIZING THEREOF

(71) Applicant: Georgia Tech Research Corporation, Atlanta, GA (US)

(72) Inventors: Seth Marder, Atlanta, GA (US); Junxiang Zhang, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 14/609,491

(22) Filed: Jan. 30, 2015

(65) Prior Publication Data

US 2015/0218115 A1    Aug. 6, 2015

Related U.S. Application Data

(60) Provisional application No. 61/934,283, filed on Jan. 31, 2014.

(51) Int. Cl.
| | | |
|---|---|---|
| *C07D 285/14* | (2006.01) | |
| *C07D 241/42* | (2006.01) | |
| *C07D 249/18* | (2006.01) | |
| *H01L 51/00* | (2006.01) | |
| *H01L 51/50* | (2006.01) | |

(52) U.S. Cl.
CPC ............ *C07D 285/14* (2013.01); *C07D 241/42* (2013.01); *C07D 249/18* (2013.01); *H01L 51/0036* (2013.01); *H01L 51/0071* (2013.01); *H01L 51/5072* (2013.01)

(58) Field of Classification Search
CPC ..................................................... C07D 285/14

USPC ............................................. 546/36; 544/353
See application file for complete search history.

(56) References Cited

PUBLICATIONS

Lautens et al., Chem. Rev. (2007), vol. 107, pp. 174-238.*
Cited in the spec. pp. 8, line 20.*
Alberico, et al., "Aryl-aryl bond formation by transition-metal-catalyzed direct arylation", Chem. Rev., 107:174-238 (2007).
Burmester and Faust, "A Reliable Route to 1,2-Diamino-4,5-phthalodinitrile", Synthesis, 8:1179-81 (2008).
Shao, et al., "Linear and star-shaped pyrazine-containing acene dicarboximides with high electron-affinity", Org. Biomol. Chem., 10:7045; 2-(2012).
Tan and Hartwig, "Assessment of the intermediacy of arylpalladium carboxylate complexes in the direct arylation of benzene: evidence for C—H bond cleavage by "ligandless" species", J. Am. Chem. Soc., 133:3308-11 (2011).
Vagin, et al., "Synthesis and Properties of an Unsymmetrical Triazole-Functionalized (Phthalocyaninato)zinc Complex", Eur. J. Org. Chem., 15:3271-8 (2005).
Wang, et al., "A new isoindigo-based molecule with ideal energy levels for solution-processable organic solar cells", Dyes Pigm, 98(1): 11-16 (2013).
Zhou, et al., "Rational Design of High Performance Conjugated Polymers for Organic Solar Cells", Macromolecules, 45(2):607-632 (2012).

* cited by examiner

*Primary Examiner* — Taofiq A Solola
(74) *Attorney, Agent, or Firm* — Pabst Patent Group LLP

(57) ABSTRACT

Various materials and polymers having electron deficient moieties and methods of synthesizing thereof are described herein. Specifically, a C—H bond activation method is disclosed wherein an electron deficient group having one or more activated C—H bonds is coupled to one or more aryl groups to afford materials or polymers which may be used in organic electronic and photonic applications.

14 Claims, 7 Drawing Sheets

MATERIALS HAVING ELECTRON DEFICIENT MOIETIES AND METHODS OF SYNTHESIZING THEREOF

CROSS-REFERENCE TO RELATED APPLICATIONS

This application claims the benefit of U.S. Ser. No. 61/934,283, filed on Jan. 31, 2014, which is incorporated herein in its entirety.

STATEMENT REGARDING FEDERALLY SPONSORED RESEARCH

This invention was made with government support under Grant Award No. CHE-1205646 awarded by the National Science Foundation. The government has certain rights in the invention.

FIELD OF THE INVENTION

The present invention generally relates to materials having electron deficient moieties and methods of synthesizing such materials.

BACKGROUND OF THE INVENTION

Electron deficient molecular moieties are important in organic electron and photonic materials for optoelectronic applications such as in organic light emitting diodes (OLED), organic photovoltaics (OPV), dye sensitized solar cells (DSSC), organic field effect transistors (OFET), and the like.

Electron deficient moieties can be used to adjust the properties of materials to, for example: match the properties of other materials present in a device (e.g., work function of electrodes); shift the wavelength at which the material absorbs (e.g., $\lambda_{max}$); provide highly electron deficient materials that may function as electron transport materials while being relatively stable to oxygen; and so on.

Often, in order to incorporate such electron deficient moieties into materials, one or more organometallic coupling reactions, such as Stille coupling, Suzuki coupling, Kumada coupling, or Heck coupling can be used. However, methods of incorporating electron deficient moieties into materials using such coupling methodologies generally suffer from: the coupling partner (e.g., organometallic or halide/pseudohalide containing derivative) having the electron deficient moiety being unstable itself (e.g., electron deficient tin (Stille) reagents) and/or the electron deficient moiety being difficult to synthesize since they either often require lithiation of an electron deficient species that itself may decompose in the presence of nucleophilic lithium reagents or require halogenation of the electron deficient compound, which requires harsh, environmentally harmful, and sometimes ineffective halogenation conditions.

Challenges and difficulties remain in the synthesis of electron-deficient materials using traditional cross-coupling reactions (i.e., Stille, Suzuki, Kumada, Heck).

Thus, there exists a need for development of materials having new electron deficient moieties which can be synthesized using alternative and relatively mild reaction methods and/or processes.

Therefore, it is an object of the invention to provide materials and polymers having electron deficient moieties which may be used as organic electronic and photonic materials.

It is a further object of the invention to provide relatively mild reaction methods for synthesizing such materials and polymers.

SUMMARY OF THE INVENTION

Various embodiments of methods for the preparation of materials having electron deficient moieties and examples of materials prepared using such methods are described herein.

According to one embodiment a C—H bond activation method is provided including a first C—H activated coupling of a dicyanobenzodiimine with a first aryl group, wherein the dicyanobenzodiimine has the following structure:

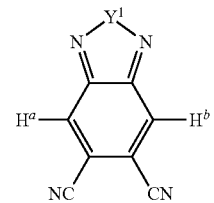

wherein $Y^1$ is selected from the group consisting of O, S, Se, $NR^1$, and $C(R^1)=C(R^1)$; and $R^1$ is independently selected at each occurrence from the group consisting of hydrogen, halogen, an alkyl group, a heteroalkyl group, an aryl group, or a heteroaryl group, and whereby a covalent bond is formed between the first aryl group and the dicyanobenzodiimine, such that $H^a$ is substituted by the first aryl group.

In some embodiments, the method further includes a second C—H activated coupling reaction of the dicyanobenzodiimine with a second aryl group, whereby a covalent bond is formed between the second aryl group and the dicyanobenzodiimine, such that $H^b$ is substituted with the second aryl group.

In another embodiment the method includes a C—H activated coupling between a dicyanoaryl compound with an aryl group. In one embodiment the method includes activating a C—H bond of a dicyanoaryl compound such that the H is substituted by a carbon atom of an aryl group.

In yet another embodiment the method includes reacting a dicyanoaryl compound having at least two C—H active groups with an aryl group having at least two metal-labile bonds (X—Ar—X; X representing, for example, a halogen, triflate, or tosylate group), whereby a polymer is formed.

Another embodiment provides a dicyanobenzodiimine compound having the following formula and is synthesized according to the methods disclosed herein.

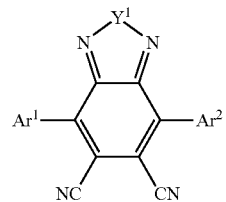

wherein $Y^1$ is selected from the group consisting of O, S, Se, $NR^1$, and $C(R^1)=C(R^1)$; $R^1$ is independently selected at each occurrence from hydrogen, halogen, an alkyl group, a heteroalkyl group, an aryl group, or a heteroaryl group; $Ar^1$ is an aryl group or a heteroaryl group; and $Ar^2$ is an aryl group or a heteroaryl group. In some embodiments, $Ar^1$ and $Ar^2$ groups may be identical or alternatively they may be different.

DETAILED DESCRIPTION OF THE INVENTION

I. Definitions

Figure 1:
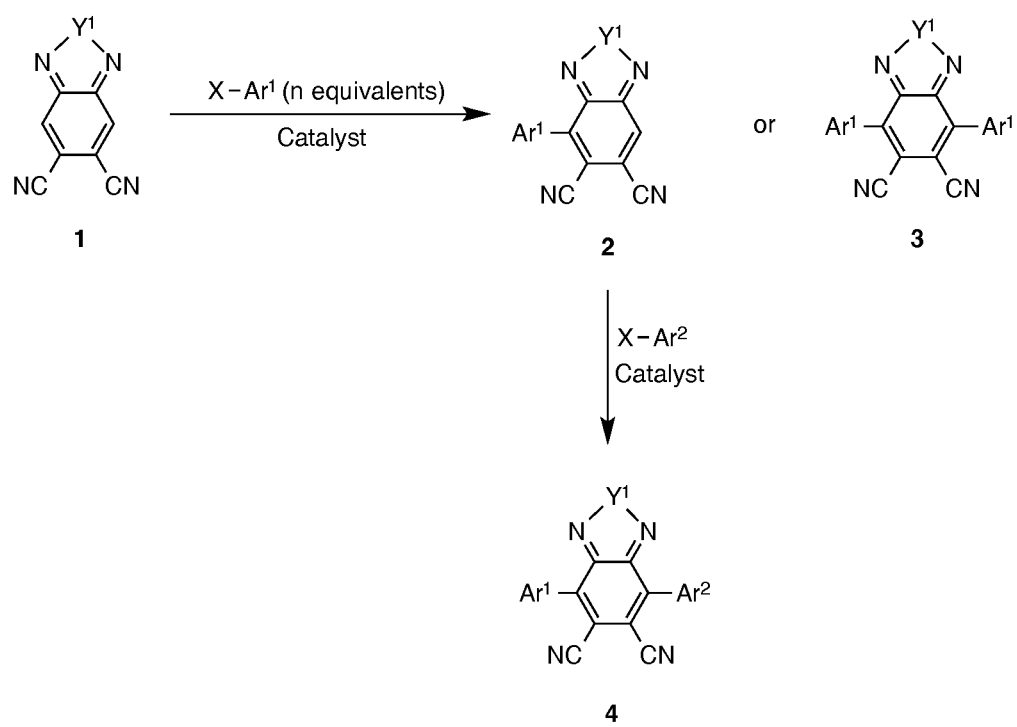
FIG. 1 shows a reaction scheme wherein a dicyanobenzodiimine compound (1) is coupled to an aryl group ($X$—$Ar^1$) using a C—H bond activation method to afford a mono-substituted compound (2) or a symmetrically di-substituted compound (3). A second coupling of a mono-substituted compound (2) with a second aryl group ($X$—$Ar^2$) using C—H bond activation may be performed to afford an unsymmetrical di-substituted compound (4).

"Alkyl," as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), preferably 20 or fewer, more preferably from about 10 to 20. If the alkyl is unsaturated, the alkyl chain generally has from 2-30 carbons in the chain, preferably from 2-20 carbons in the chain, more preferably from 10-20 carbons in the chain. Likewise, preferred cycloalkyls have from 3-20 carbon atoms in their ring structure, preferably from 3-10 carbons atoms in their ring structure, most preferably 5, 6 or 7 carbons in the ring structure.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

"Aryl", as used herein, refers to $C_5$-$C_{10}$ membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like.

Those aryl groups having heteroatoms in the ring structure may also be referred to as "heteroaryls" or "heteroarenes." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl."

"Electron donor group," as used herein, generally refers to a moiety which is relatively electron rich and has a low ionization potential.

"Electron acceptor group," as used herein, generally refers to a moiety which is relatively electron poor and has a high electron affinity.

Exemplary "electron donor and electron acceptor groups," or moieties, are well-known in that art, see for example: Zhou, H.; Yang, L.; You, W. *Macromolecules* 2012, 45, 607-632, which is incorporated herein by reference.

"Intermediate," as used herein, refers to a chemical substance or compound that is necessarily produced or synthesized during the synthesis of a different product, substance, or compound. The intermediate may be obtained, isolated, extracted, purified, crystallized, or separated in some manner from the reaction mixture using any number of methods known in the art. The synthetic intermediate need not necessarily be obtained, isolated, extracted, purified, crystalized, or separated in any manner from the reaction mixture. The intermediate may be produced and subsequently consumed, transformed, derivatized, or reacted with to produce the desired product or to produce a different intermediate without ever obtaining, isolating, extracting, purifying, crystalizing, or separating the intermediate from the reaction mixture.

"Polymer," as used herein, refers to a molecule formed of multiple monomer units, typically having at least two or more monomeric repeat units and encompasses dimers, trimers, oligomers, dendrimers, and other known classes of polymers known in the art.

II. Methods

One C—H bond activation method includes C—H activated coupling of a dicyanobenzodiimine (see compound 1 in FIG. 1) with an aryl group. A C—H activated coupling refers to a well-known type of reaction in the art, for example see Lautens et al., *Chem. Rev.* 2007, 107, 174-238, which is incorporated herein by reference in its entirety.

Another method includes activating a C—H bond of a dicyanobenzodiimine compound such that the activated —H bond is substituted by a carbon atom of an aryl group.

Still another method includes forming a covalent bond between a first carbon atom of a dicyanobenzodiimine compound and a second carbon atom of an aryl group, wherein the first carbon prior to the coupling reaction is bonded to at least one hydrogen, and whereby post-coupling the hydrogen is substituted by a second carbon atom of the aryl group. The second carbon atom need not necessarily be a part of the aromatic π-system of the aryl group, but can be a substituent present on the aryl group such as, for example, part of an alkene substituent of a styrene (e.g., such as in a Heck coupling).

Another method includes reacting a coupling partner (i.e., typically the aryl-containing group), having at least one metal-labile bond having a first carbon atom, with a dicyanobenzodiimine compound having at least one activated bond. The at least one activated bond has a first active carbon atom bonded to a hydrogen atom (C—H), whereby the hydrogen atom bonded to the first active carbon atom is substituted by the first carbon atom of the coupling partner. Typically, the metal-labile bond is labile by oxidative insertion or addition of a metal (such as Pd or Pt, for example) into the bond, e.g., when the metal-labile bond includes the first carbon and, for example, a halogen, triflate, or tosylate group bonded to the first carbon. Such oxidative addition or insertion reactions are well-known in the art of "C—H activation catalysis," see for example Tan, Y.; Hartwig, J. F., *J. Am. Chem. Soc.* 2011, 133, 3308-3311, which is incorporated herein by reference in its entirety.

Referring now to FIG. 1, an exemplary method is represented by the scheme shown including reacting a dicyanobenzodiimine (compound 1), or derivative thereof, with at least one aryl group ($Ar^1$) having at least one labile bond (i.e., $Ar^1$—X) into which a metal atom of a catalyst can oxidatively add/insert into, the labile bond including an X group (wherein X may be, but is not limited to being for example a halogen, triflate, tosylate group), whereby an activate hydrogen atom (C—H) of the dicyanobenzodiimine is substituted by the aryl group ($Ar^1$) upon coupling.

In certain embodiments, the dicyanobenzodiimine is reacted with at least two $Ar^1$ groups, whereby at least two activated hydrogen atoms of the dicyanobenzodiimine are substituted with at least two $Ar^1$ groups (FIG. 1, compound 3) producing a symmetrically substituted compound. In another embodiment, the method includes: 1) reacting a dicyanobenzodiimine having a first activated hydrogen atom and a second activated hydrogen atom with a first aryl group ($Ar^1$), whereby the first hydrogen atom of the dicyanobenzodiimine is substituted by the first aryl group to give an intermediate (FIG. 1, compound 2); and 2) reacting the intermediate (2) with a second aryl group ($Ar^2$), whereby the second activated hydrogen atom is substituted by the second aryl group to afford an asymmetrically substituted compound (FIG. 1, compound 4). In preferred embodiments, the X group is a halogen, triflate, or tosylate, or other group which can undergo oxidative addition/insertion by a metal, such as a transition metal present in the catalyst which may include palladium, platinum, copper, or other transitional metals.

Again referring to FIG. 1, $Y^1$ may include a Group VII atom, a Group VIII atom, or carbon atom. In one embodiment, $Y^1$ is O, S, Se,

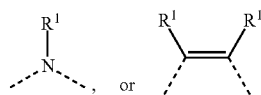

wherein "- - -" represents bonds to the dicyanobenzodiimine and $R^1$ is independently selected at each occurrence from H, halogen, an alkyl group, a heteroalkyl group, an aryl group, or a heteroaryl group. The aryl groups $Ar^1$ and $Ar^2$ may aryl or heteroaryl groups and may be relatively electron rich (e.g., a electron donor) or relatively electron poor (e.g., an electron acceptor) as compared to the dicyanobenzodiimine.

Figure 2:
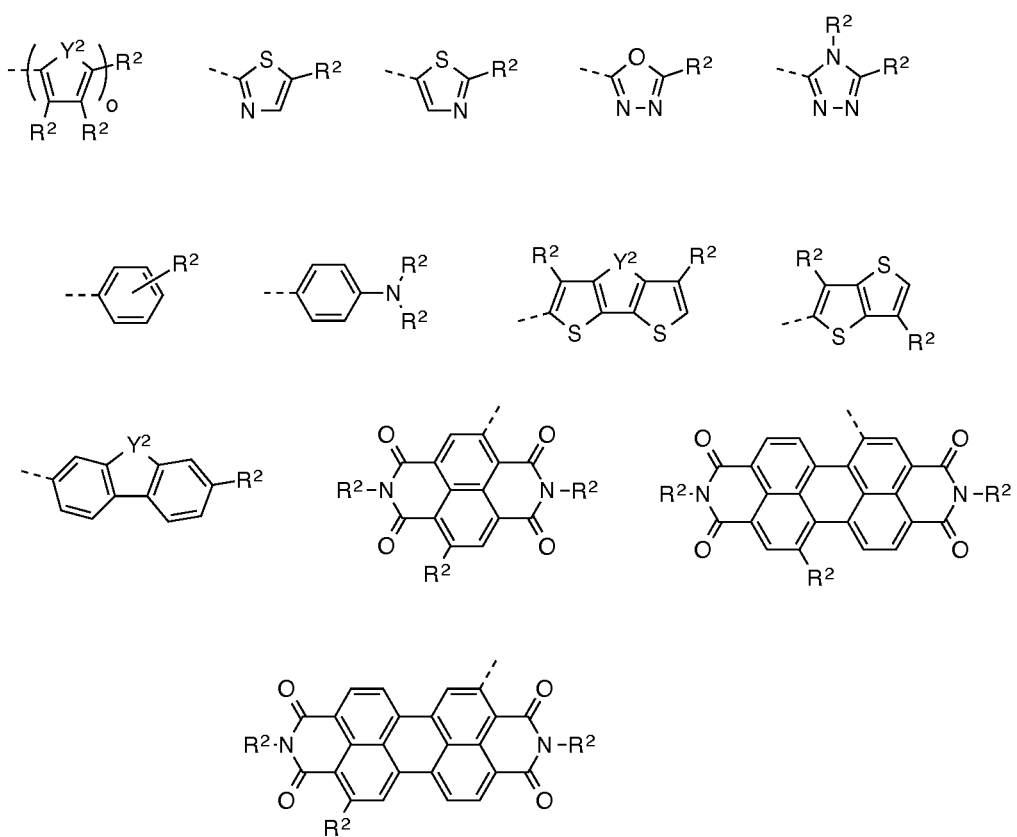
FIG. 2 shows exemplary aryl groups that may be coupled to a dicyanobenzodiimine or dicyanoaryl group wherein "- - -" denotes the bond formed between the second aryl group and a dicyanobenzodiimine or dicyanoaryl group; $Y^2$ is independently selected at each occurrence from the group consisting of O, S, Se, Ge, $C(R^1)_2$, $Si(R^1)_2$, $Ge(R^1)_2$, and $NR^1$; $R^1$ is independently selected at each occurrence from the group consisting of hydrogen, halogen, an alkyl group, a heteroalkyl group, an aryl group, and a heteroaryl group; $R^2$ is independently selected at each occurrence from the group consisting of hydrogen, halogen, an alkyl group, a heteroalkyl group, an aryl group, and a heteroaryl group; and o has an integer value from 1-4.

Examples of $Ar^1$ and $Ar^2$ aryl and heteroaryl groups are shown in FIG. 2, wherein the dashed line ("- - -") represents the bond to the dicyanobenzodiimine upon coupling. $Y^2$ may include, for example, O, S, Se,

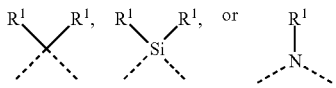

wherein $R^1$ may independently be selected from an H, halogen, an alkyl group, a heteroalkyl group, an aryl group, or a heteroaryl group and $R^2$ may independently be selected from a hydrogen, halogen, an alkyl group, a heteroalkyl group, an aryl group, or a heteroaryl group. $R^2$ and $R^2$ groups may be bonded to other atoms present in the molecule to form rings. For example, in the structure shown below

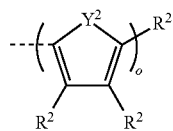

the $R^2$ groups on the lower half of the fragment may include

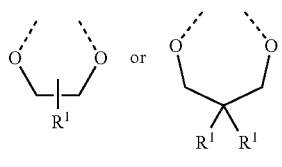

"EDOT"    "ProDOT"

wherein $R^1$ is independently selected at each occurrence from a hydrogen, halogen, an alkyl group, a heteroalkyl group, an aryl group, or a heteroaryl group. The methods described herein may also include other couplings so as to form a polymer.

In one embodiment of the method a first C—H activated coupling of a dicyanobenzodiimine with a first aryl group is performed, wherein the dicyanobenzodiimine has the structure:

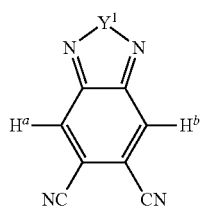

wherein $Y^1$ is selected from the group consisting of O, S, Se, $NR^1$, and $C(R^1)=C(R^1)$; $R^1$ is independently selected at each occurrence from hydrogen, halogen, an alkyl group, a heteroalkyl group, an aryl group, or a heteroaryl group, and whereby a covalent bond is formed between the first aryl group and the dicyanobenzodiimine such that Ha is substituted by the first aryl group. The first aryl group may include, for example, any of the aryl groups shown in FIG. 2, wherein "- - -" denotes the bond formed between the first aryl group and the dicyanobenzodiimine upon coupling; $Y^2$ independently selected at each occurrence from O, S, Se, Ge, $C(R^1)_2$, $Si(R^1)_2$, $Ge(R^1)_2$, or $NR^1$; $R^1$ independently selected at each occurrence from a hydrogen, halogen, an alkyl group, a heteroalkyl group, an aryl group, or a heteroaryl group; $R^2$ is independently selected at each occurrence from a hydrogen, halogen, an alkyl group, a heteroalkyl group, an aryl group, or a heteroaryl group; and o has an integer value from 1-4. In one embodiment, the first aryl group includes a structure as shown below:

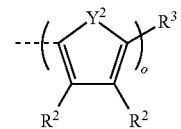

wherein $Y^2$ is a sulfur atom; $R^2$ group(s) form a heterocyclic ring, and $R^3$ is selected from a hydrogen, halogen, an alkyl group, a heteroalkyl group, an aryl group, or a heteroaryl group; and o has an integer value from 1-3. Further examples of the first aryl group are:

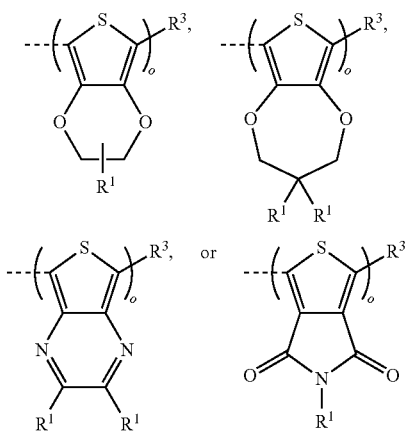

wherein $R^1$ is independently at each occurrence from a hydrogen, halogen, an alkyl group, a heteroalkyl group, an aryl group, or a heteroaryl group; $R^3$ is independently selected at each occurrence from a hydrogen, halogen, an alkyl group, a heteroalkyl group, an aryl group, or a heteroaryl group; and o has an integer value from 1-3.

In certain embodiments, the first aryl group incudes an electron donor. Exemplary electron donor groups are:

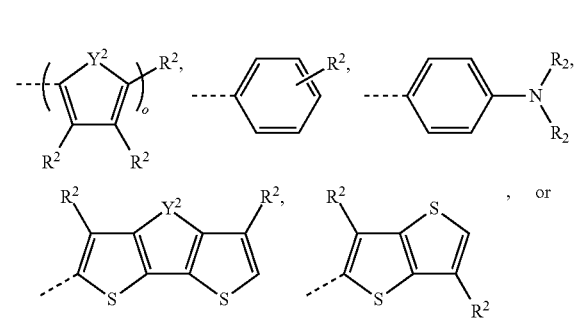

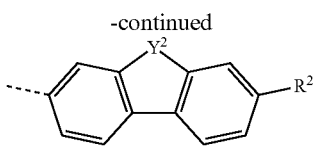

wherein "- - -" denotes the bond formed between the first aryl group and the dicyanobenzodiimine; $Y^2$ is independently selected at each occurrence from O, S, Se, Ge, $C(R^1)_2$, $Si(R^1)_2$, $Ge(R^1)_2$, or $NR^1$; $R^1$ is independently selected at each occurrence from a hydrogen, halogen, an alkyl group, a heteroalkyl group, an aryl group, or a heteroaryl group; $R^2$ is independently selected at each occurrence from a hydrogen, halogen, an alkyl group, a heteroalkyl group, an aryl group, or a heteroaryl group; and o has an integer value from 1-4.

In some embodiments, the first aryl group includes an electron acceptor. Exemplary electron acceptor groups are:

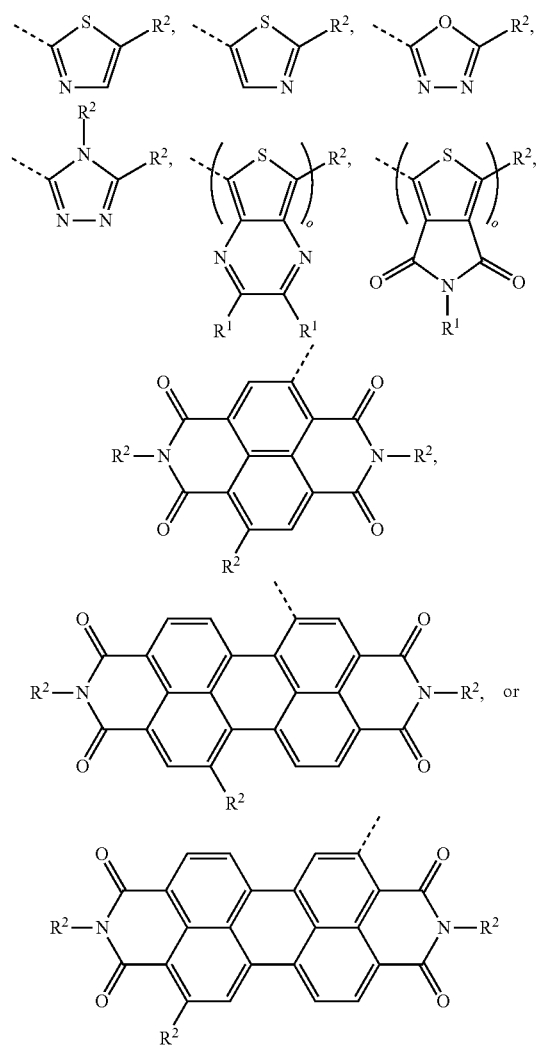

wherein "- - -" denotes the bond formed between the first aryl group and the dicyanobenzodiimine; $R^1$ is independently selected at each occurrence from a hydrogen, halogen, an alkyl group, a heteroalkyl group, an aryl group, or a heteroaryl group; $R^2$ is independently selected at each occurrence from a hydrogen, halogen, an alkyl group, a heteroalkyl group, an aryl group, or a heteroaryl group; and o has an integer value from 1-4.

The methods described herein may further include a second C—H activated coupling of the dicyanobenzodiimine with a second aryl group, whereby a covalent bond is formed between the second aryl group and the dicyanobenzodiimine such that $H^b$ is substituted by the second aryl group. The first aryl group and the second aryl group may independently includes any of the aryl groups shown in FIG. 2, wherein "- - -" denotes the bond formed between the aryl group and the dicyanobenzodiimine; $Y^2$ is independently selected at each occurrence from O, S, Se, Ge, $C(R^1)_2$, $Si(R^1)_2$, $Ge(R^1)_2$, or $NR^1$; $R^1$ is independently selected at each occurrence from a hydrogen, halogen, an alkyl group, a heteroalkyl group, an aryl group, or a heteroaryl group; $R^2$ is independently selected at each occurrence from a hydrogen, halogen, an alkyl group, a heteroalkyl group, an aryl group, or a heteroaryl group; and o has an integer value from 1-4.

In one embodiment, the first aryl group and the second aryl group are identical and form a symmetrically substituted compound. In another embodiment, the first aryl group and the second aryl group are different and form an asymmetrically substituted compound. In yet another embodiment, the first aryl group and the second aryl group independently includes electron donors, where examples of electron donors are as described above. In another embodiment, the first aryl group and the second aryl group independently include electron acceptors, where examples of electron acceptors are as described above. In one embodiment, the first aryl group is an electron acceptor and the second aryl group is an electron donor. In yet another embodiment, the first aryl group is an electron donor and the second aryl group is an electron acceptor. The electron donors and acceptor groups may be as described above or chosen from among the many of those known to those skilled in the art.

In one embodiment, the methods described herein can be used to synthesize a dicyanobenzodiimine compound having the formula:

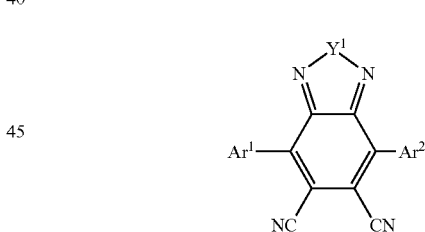

wherein $Y^1$ is selected from O, S, Se, $NR^1$, or $C(R^1)=C(R^1)$; $R^1$ is independently selected at each occurrence from a hydrogen, halogen, an alkyl group, a heteroalkyl group, an aryl group, or a heteroaryl group; $Ar^1$ is an aryl group or a heteroaryl group; and $Ar^2$ is an aryl group or a heteroaryl group such as those shown above. In certain embodiments, the $Ar^1$ and $Ar^2$ groups may be independently selected at each occurrence from those groups shown in FIG. 2. In yet another embodiment, $Ar^1$ and $Ar^2$ are independently selected from an electron donor or an electron acceptor group as described herein or from one of the many known groups found in the art.

Figure 3:
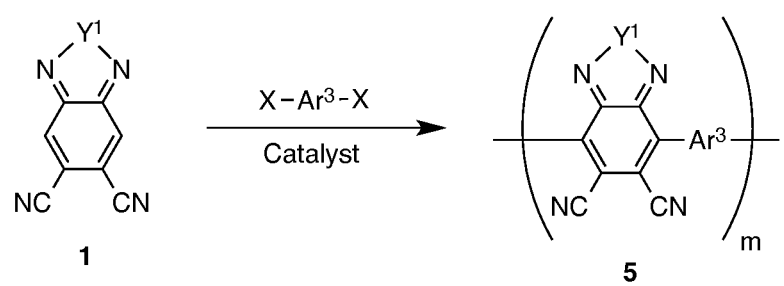
FIG. 3 shows a reaction scheme wherein a dicyanobenzodiimine (1) having at least two C—H active groups is coupled with an aryl group having at least two metal-labile bonds (i.e., $X$—$Ar^3$—$X$; wherein X may be for example a halogen, triflate, or tosylate), to form a polymer (5) (e.g., m>2).

In yet another embodiment of the C—H activated methods disclosed, a C—H activated polymerization of a dicyanobenzodiimine with an aryl group may be performed. Referring now to FIG. 3, a method including reacting a dicyanobenzodiimine (see FIG. 3, compound 1) having at least two C—H active groups with an aryl group having at least two metal-labile bonds (i.e., X—Ar³—X; wherein X may be for example a halogen, triflate, or tosylate), whereby a polymer (5) is formed (e.g., m>2).

Figure 4:
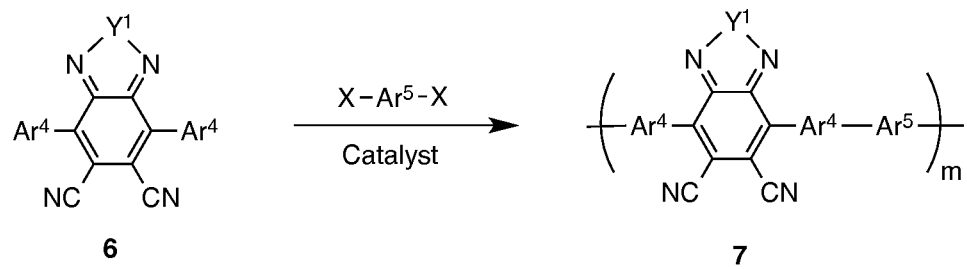
FIG. 4 shows a reaction scheme wherein a dicyanobenzodiimine (6) substituted a first and a second aryl group ($Ar^4$), wherein each of the first and second aryl groups has at least one activated C—H bond, is reacted with a third aryl group having at least two metal-labile bonds (i.e., $X$—$Ar^5$—$X$; wherein X may be for example a halogen, triflate, or tosylate), and the coupling reaction produces a polymer (7).
Figure 5:
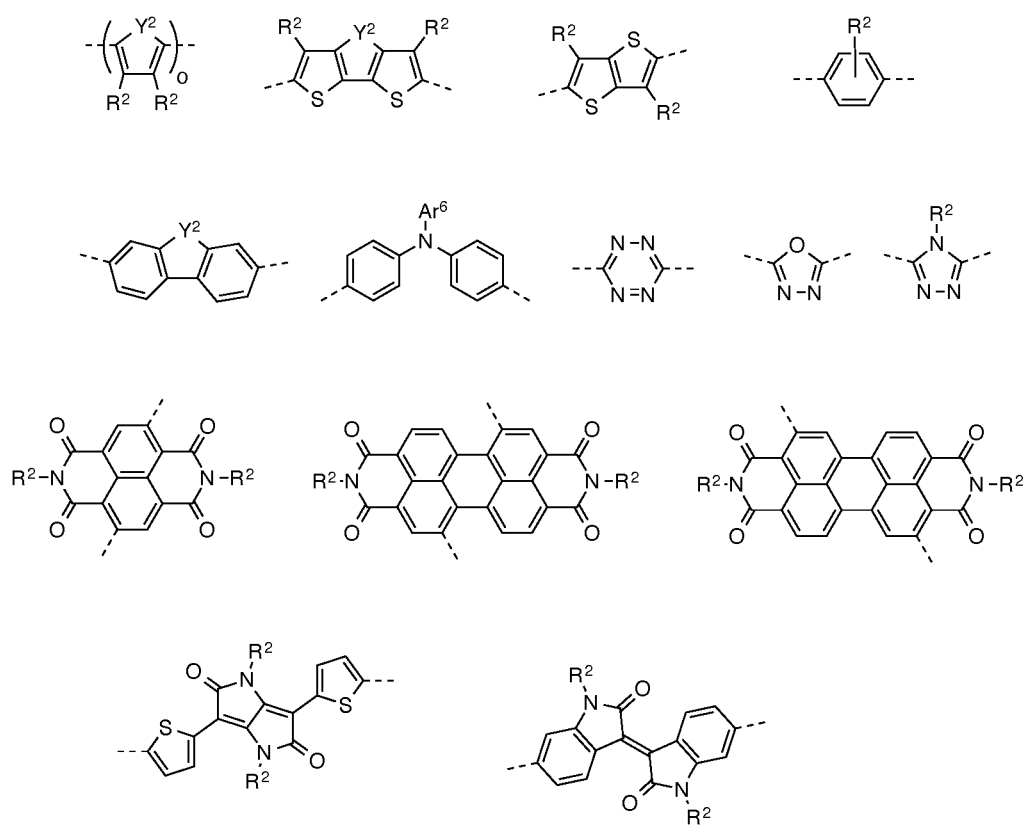
FIG. 5 shows exemplary aryl groups that may be coupled to a dicyanobenzodiimine or dicyanoaryl group wherein "- - -" denotes a bond formed between the aryl group and a dicyanobenzodiimine or dicyanoaryl group; $Y^2$ is independently selected at each occurrence from the group consisting of O, S, Se, Ge, $C(R^1)_2$, $Si(R^1)_2$, $Ge(R^1)_2$, and $NR^1$; $R^1$ is independently selected at each occurrence from the group consisting of hydrogen, halogen, an alkyl group, a heteroalkyl group, an aryl group, and a heteroaryl group; $R^2$ is independently selected at each occurrence from the group consisting of hydrogen, halogen, an alkyl group, a heteroalkyl group, an aryl group, and a heteroaryl group; $Ar^6$ is selected from the group consisting of hydrogen, halogen, an alkyl group, a heteroalkyl group, an aryl group, and a heteroaryl group; and o has an integer value from 1-4.

In yet another embodiment a C—H activated polymerization method is disclosed. Referring to FIG. 4, the method includes reacting a dicyanobenzodiimine having a first and a second aryl group (i.e., Ar⁴), wherein each of the first and second aryl groups has at least one activated C—H bond (compound 6), and reacting it with a third aryl group having at least two metal-labile bonds (X—Ar⁵—X; wherein X may be for example a halogen, triflate, or tosylate), whereby the coupling reaction produces a polymer (7). The Ar³, Ar⁴, and Ar⁵ groups may independently be selected from any of the groups described above or as shown in FIG. 5. $Y^1$, $Y^2$, $R^1$, and $R^2$ groups may independently be selected as described from any of the groups already described above.

Another embodiment of method involves a C—H activated coupling of a dicyanoaryl compound (see FIG. 7, compound 11) with an aryl group. One embodiment of the method includes activating a C—H bond of a dicyanoaryl compound so that the activate H is substituted by a carbon atom of an aryl group. In one embodiment, the method includes reacting a dicyanoaryl compound with at least one aryl group, wherein the aryl group has at least one labile bond into which a metal atom of a catalyst (as described above) can oxidatively insert or add, the labile bond including an X group (wherein X, may be for example a halogen, triflate, or tosylate), whereby a hydrogen atom of the dicyanoaryl is substituted by the aryl group ($Ar^1$). The X group and $Ar^1$ group may be selected as described above. The dicyanoaryl compound may include, for example, 1,2-dicyanobenzene; 3,4-dicyanothiophene; 2,3-dicyanonaphthalene; and the like. The dicyanoaryl compound may be further substituted with one or more electron withdrawing groups (i.e., independently at each occurrence of $R^3$). Electron withdrawing groups for substitution may include, but are not limited to, for example, fluoro, formyl, carboxyl, ester, cyano, nitro groups, and the like. The dicyanoaryl compound may be, for example, 1,2,4,5-tetracyanoebenzene; 1,2-difluoro-4,5-dicyanobenzene; 1,4-difluoro-2,5-dicyanobenzene; 4,5-dicyanophthalic acid and ester derivatives thereof; 2,5-dicyanoterephthalic acid and ester derivatives thereof; 4,5-dicyanophthalaldehyde; 4,5-dicyanophthalimide; and the like.

Figure 7:
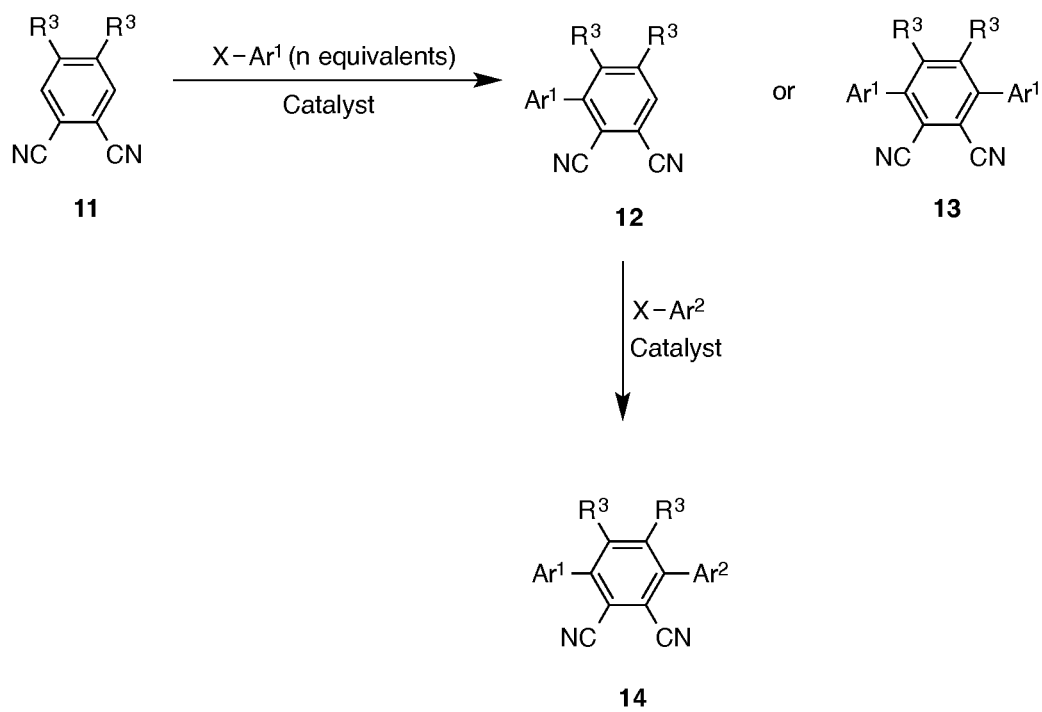
FIG. 7 shows a reaction scheme wherein a dicyanoaryl compound (11) is coupled to an aryl group ($X$—$Ar^1$) using a C—H bond activation method to afford a mono-substituted compound (12) or a symmetrically di-substituted compound (13). A second coupling of a mono-substituted compound (2) with a second aryl group ($X$—$Ar^2$) using C—H bond activation may be performed to afford an unsymmetrical di-substituted compound (14).

Still referring to FIG. 7, another embodiment of the method includes forming a bond between a first carbon atom of a dicyanoaryl compound (compound 11) and a second carbon atom of an aryl group ($Ar^1$), wherein the first carbon of the dicyanoaryl compound is bonded to at least one hydrogen, and whereby the hydrogen is substituted by the second carbon atom of the aryl group (see compound 12). $R^3$ may be selected, for example, from a hydrogen, halogen, carbonyl, a cyano group, or a nitro group. In one embodiment, $R^3$ includes an electron withdrawing group, for example, an fluorine, carbonyl, a cyano group, or a nitro group.

In one embodiment of the method, the process includes reacting a coupling partner having at least one metal-labile bond including a first carbon atom (e.g., X—$Ar^1$) with a dicyanoaryl compound having at least one active C—H bond including a carbon atom bonded to a hydrogen atom, whereby the hydrogen atom bonded to the active carbon atom is substituted by the first carbon atom of the coupling partner. In one embodiment, the dicyanoaryl compound is reacted with at least two $Ar^1$ groups, whereby at least two activated hydrogen atoms of the dicyanoaryl compound are substituted with at least two $Ar^1$ groups (see FIG. 7, compound 13). In yet another embodiment, the method includes: 1) reacting a dicyanoaryl compound having a first activated hydrogen atom and a second activated hydrogen atom with a first aryl group ($Ar^1$), whereby the first hydrogen atom of the dicyanoaryl compound is substituted by the first aryl group to give an intermediate (see FIG. 7, compound 12); and 2) reacting the intermediate with a second aryl group ($Ar^2$), whereby the second hydrogen atom is substituted with the second aryl group to afford a doubly substituted product (see FIG. 7, compound 14).

In another embodiment, the method includes reacting a dicyanoaryl compound having at least two C—H active groups with an aryl group having at least two metal-labile bonds (X—Ar—X), whereby a polymer is formed. One embodiment is a method including reacting a dicyanoaryl compound having a first and a second aryl group, wherein each of the first and second aryl has at least one active C—H bond, with a third aryl group having at least two metal-labile bonds (X—Ar—X), whereby a polymer is formed. The Ar groups may independently be as described above or as shown in FIG. 5. $Y^2$, $R^1$, and $R^2$ groups independently may be as described above. The dicyanoaryl compound may be as described above.

III. Exemplary Electron Deficient Materials

Figure 6:
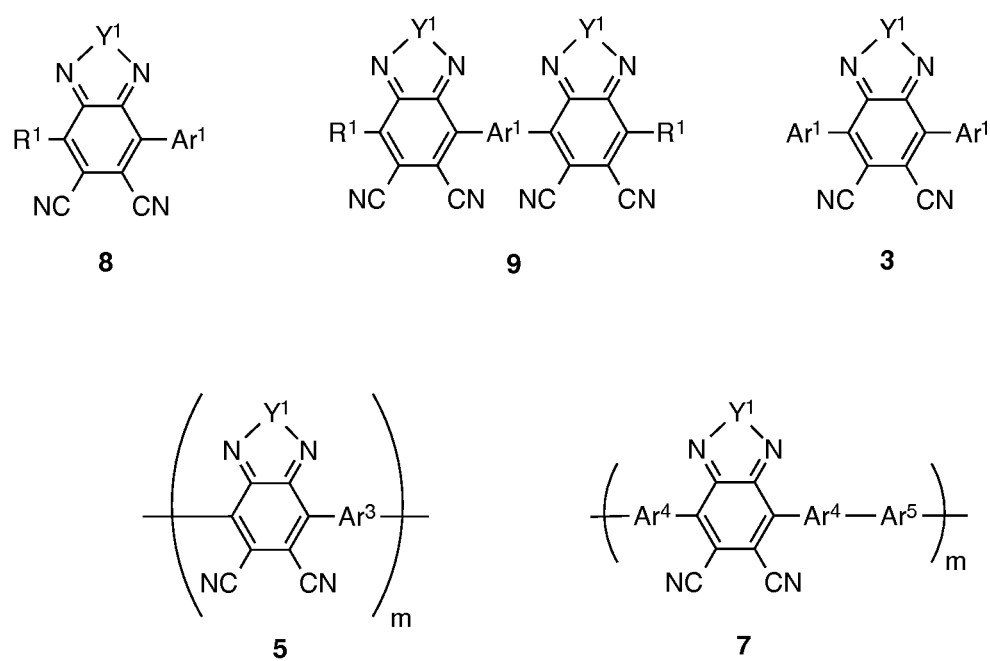
FIG. 6 shows exemplary electron deficient materials and polymers containing at least one dicyanobenzodiimine and produced via the C—H bond activation methods described.

Referring now to FIG. 6, various embodiments of the methods described herein can be utilized to afford materials including compositions of matter including at least one dicyanobenzodiimine moiety. One embodiment is a composition of matter including a dicyanobenzodiimine substituted by at least one aryl group (compound 8). Another embodiment is a composition of matter including an aryl group substituted by at least two dicyanobenzodiimines moieties (compound 9). In some embodiments, the aryl group of compound 9 may be substituted with more than two dicyanobenzodiimine moieties. For example, the aryl group of compound 9 may form the core of a dendrimer. One embodiment is a composition of matter including a dicyanobenzodiimine substituted with at least two aryl groups (compound 3). In yet another embodiment, the composition of matter including may be a polymer having one monomer that includes a dicyanobenzodiimine and another monomer that includes an aryl group. The dicyanobenzodiimine monomer and the aryl group monomer may be directly bonded together as shown in compound 5 (e.g., m>2). In another embodiment, the composition of matter includes a polymer (compound 7) having: 1) one monomer that includes a dicyanobenzodiimine substituted with at least two aryl groups ($Ar^4$); and 2) a second monomer including an aryl group ($Ar^5$) bonded to aryl groups ($Ar^4$) substituting dicyanobenzodiimines moieties.

In the various embodiments shown in FIG. 6, the $Y^1$, $Y^2$, $R^1$, and $R^2$ groups are independently selected from the groups as described above and from examples of aryl groups (e.g., $Ar^1$ to $Ar^5$ groups) as described above and/or as shown in FIG. 2 and FIG. 5.

Figure 8:
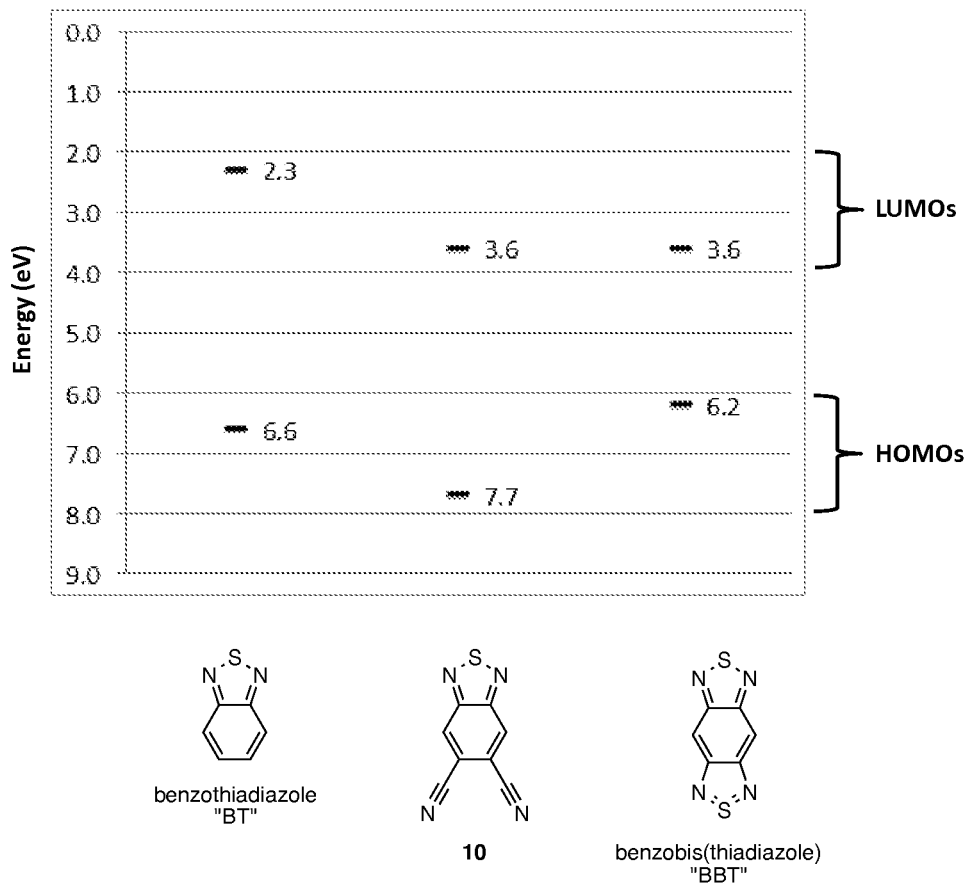
FIG. 8 is a graph showing the lowest unoccupied molecular orbital (LUMO) and highest occupied molecular orbital (HOMO) energy levels (calculated at the B3LYP/6-31G* level) in units of electron volts (left axis) for compound 10, and electron acceptors benzothiadiazole (BT) and benzobis(thiadiazole) (BBT).

Referring now to FIG. 8, theoretical calculations at the B3LYP/6-31G* level show that, for example when $Y^1$ is sulfur (compound 10), the dicyanobenzodiimine has a lowest unoccupied molecular orbital (LUMO) energy level that is very near to the LUMO energy level of the electron acceptor benzobis(thiadiazole) (BBT) and a highest occupied molecular orbital (HOMO) energy level that is below that of another electron acceptor benzothiadiazole (BT). Compositions of matter covalently incorporating dicyanobenzodiimines may be expected to be good electron acceptors with respect to both HOMO and LUMO energy levels.

One skilled in the art would recognize that compositions of matter including a dicyanobenzodiimine moiety that further includes varying amounts of relatively electron rich aryl groups such as, for example, thiophene, EDOT, ProDOT, thienothiophene, and/or diethienothiophene, and the like in combination with, or alone with relatively electron poor aryl groups including, for example, thiadiazole, oxadiazole, triazole, benzothiadiazole (BT), and/or rylenediimides and the like can have a range of properties such as, for example, moderate to strongly accepting electron affinities, moderate to very weakly donating ionization potentials, and moderate to narrow optical bandgaps that may be useful in a variety of applications such as, for example, electron-transport materials, electron accepting constituents in bulk heterojunction devices, oxygen/air stable materials, and visible to near-IR emitters in OLEDs, OFETs, OPVs, DSSCs and the like.

EXAMPLES

Materials and General Methods

Anhydrous DMSO, toluene, 1,2-dichloroethane, and acetonitrile solvents were purchased from Aldrich. Pd(OAc)$_2$, Pd(OPiv)$_2$ {OPiv=pivlate, $^t$BuCO$_2$}, and Pd(CF$_3$COO)$_2$ were purchased from Strem Chemicals. 4,5-Dinitro-1,2-phenylenediamine, 3,4-hexadione, pivalic acid and P$^t$Bu$_2$Me.HBF$_4$ were purchased from Acros and Alfa Aesar, respectively. Solvents and reagents were used as received. 4,5-Dibromo-1,2-benzenediamine was prepared according to Shao, J.; Chang, J.; Chi, C. *Org. Biomol. Chem.* 2012, 10, 7045; 2-trimethylstannane-5-(2-ethylhexyl)thiophene was prepared according to Wang, T.; Chen, Y.; Bao, X.; Du, Z.; Guo, J.; Wang, N.; Sun, M.; Yang, R. *Dyes Pigm.* 2013, 98, 11; 5,6-dicyano-1H-benzotriazole was prepared according to Vagin, S.; Frickenschmidt, A.; Kammerer, B.; Hanack, M. *Eur. J. Org. Chem.* 2005, 2005, 3271; and 5,6-dicyano[2,1,3]benzothiadiazole (DCBT, 1) was prepared according to Burmester, C.; Faust, R. *Synthesis* 2008, 2008, 1179.

Example 1

Arylation on benzo[c][1,2,5]thiadiazole-5,6-dicarbonitrile (DCBT) by aryl bromide

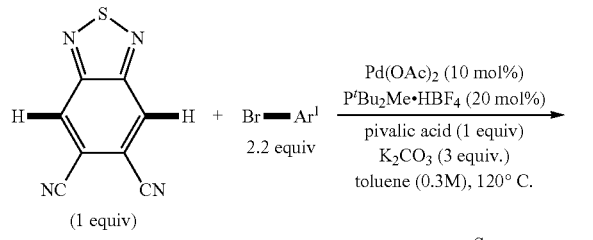

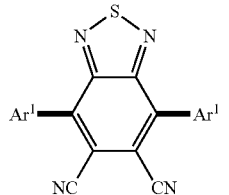

To an oven-dried 5 mL collared tube (CEM Corp., Prod #89079-404) containing a stirring bar, Pd(OAc)$_2$ (2.8 mg, 0.013 mmol), P$^t$Bu$_2$Me.HBF$_4$ (6.2 mg, 0.025 mmol), pivalic acid (12.3 mg, 0.125 mmol), benzo[c][1,2,5]thiadiazole-5,6-dicarbonitrile (DCBT, 21.5 mg, 0.125 mmol), potassium carbonate (54 mg, 0.38 mmol), and arylbromide (0.275 mmol) were sequentially added under a flow of N$_2$. Anhydrous toluene (0.4 mL) was added and a septum-cap was crimped on the vial to form a seal. The reaction mixture was heated in a 120° C. oil bath for 3-10 h until the reaction was judged complete by examining aliquots with GC/MS or $^1$H NMR spectroscopy. The resulting mixture was cooled to room temperature and filtered through a layer of Celite® (5 mL) using dichloromethane (DCM). The filtrate was concentrated under reduced pressure and the residue was purified by column chromatography on silica gel (eluent: hexanes/DCM) affording the corresponding diarylated product.

Various aryl bromides having different electronic properties (i.e. electron-rich or -poor) were used to obtain the following bis-arylated products. In addition, heteroarenes were also used and well tolerated. Furthermore, a broad range of functional groups, including aryl ester, aldehyde, and trimethylsilyl, were compatible under the reaction conditions.

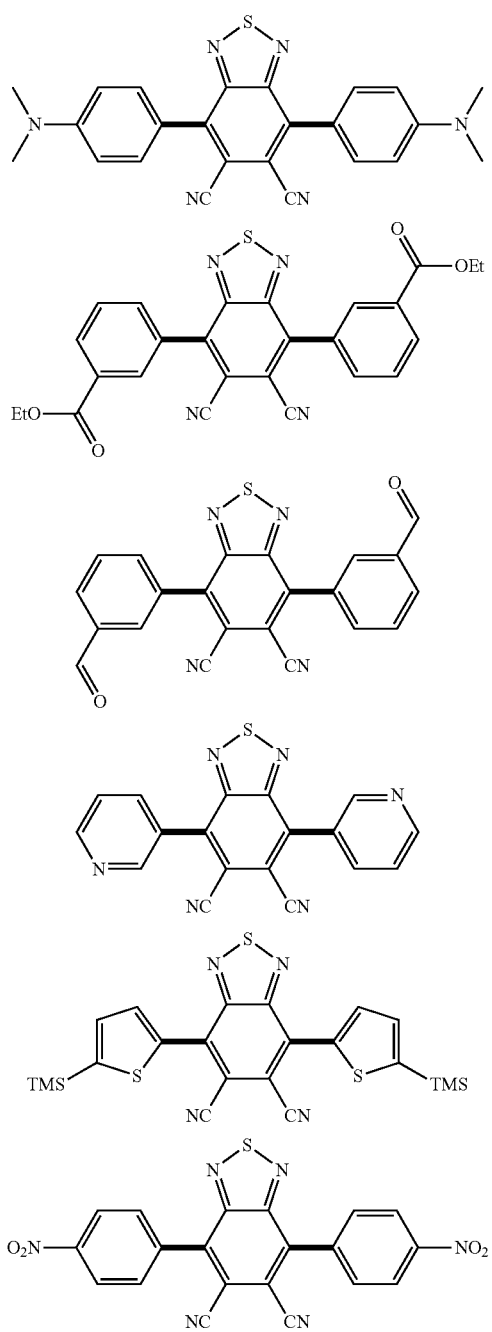

Example 2

Arylation on 2,3-diethylquinoxaline-6,7-dicarbonitrile (DCQ) by aryl bromide

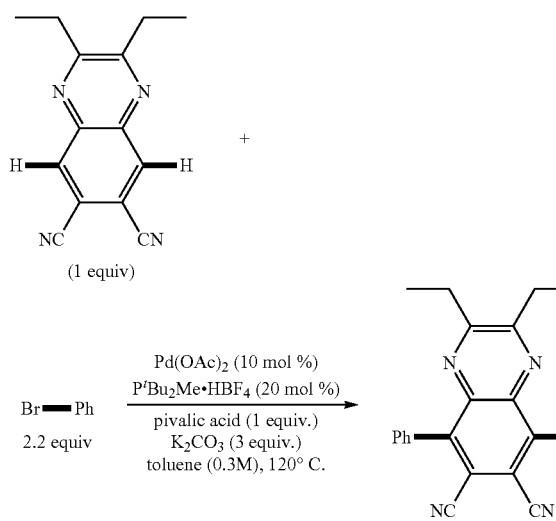

To an oven-dried 5 mL collared tube (CEM Corp., Prod #89079-404) containing a stirring bar, Pd(OAc)$_2$ (2.8 mg, 0.013 mmol), P$^t$Bu$_2$Me.HBF$_4$ (6.2 mg, 0.025 mmol), pivalic acid (12.3 mg, 0.125 mmol), 2,3-diethylquinoxaline-6,7-dicarbonitrile (DCQ, 29.5 mg, 0.125 mmol), potassium carbonate (54 mg, 0.38 mmol), and bromobenzene (0.275 mmol) were sequentially added under a flow of N$_2$. Anhydrous toluene (0.4 mL) was added and a septum-cap was crimped on the vial to form a seal. The reaction mixture was heated in a 120° C. oil bath until the reaction was judged complete by examining aliquots with GC/MS or $^1$H NMR spectroscopy. The resulting mixture was cooled to room temperature and filtered through a layer of Celite® (5 mL) using dichloromethane (DCM). The filtrate was concentrated under reduced pressure and the residue was purified by column chromatography on silica gel (eluent: hexanes/DCM) affording the corresponding diarylated product as yellowish solid in 89%.

Example 3

Alkenylation on benzo[c][1,2,5]thiadiazole-5,6-dicarbonitrile by styrene

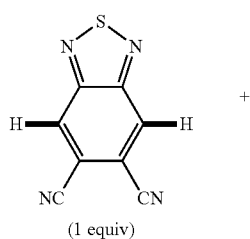

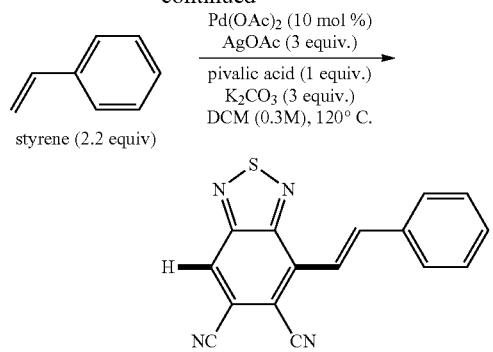

To an oven-dried 5 mL collared tube (CEM Corp., Prod #89079-404) containing a stirring bar Pd(OAc)$_2$ (2.8 mg, 0.013 mmol), AgOAc (62.6 mg, 0.375 mmol), pivalic acid (12.3 mg, 0.125 mmol), 2,3-diethylquinoxaline-6,7-dicarbonitrile (29.5 mg, 0.125 mmol), potassium carbonate (54 mg, 0.375 mmol), and stryene (28.6 mg, 0.275 mmol) were sequentially added under a flow of N$_2$. Anhydrous 1,2-dichloroethane (0.4 mL) was added and a septum-cap was crimped on the vial to form a seal. The reaction mixture was heated in a 120° C. oil bath and monitored by examining aliquots with GC/MS or $^1$H NMR spectroscopy. The resulting mixture was cooled to room temperature and filtered through a layer of Celite® (5 mL) using dichloromethane (DCM). The filtrate was concentrated under reduced pressure and the residue was purified by column chromatography on silica gel (eluent: hexanes/DCM) affording the mono-substituted product as yellowish solid in 62%.

Example 4

Arylation on 1,2,4,5-tetracyanobenzene

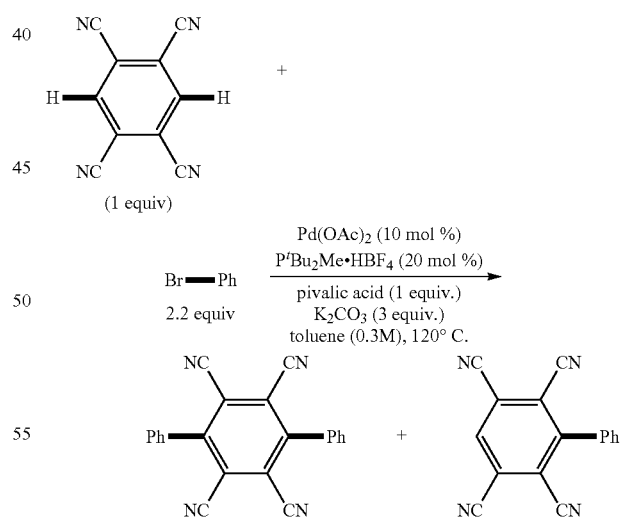

To an oven-dried 5 mL collared tube (CEM Corp., Prod #89079-404) containing a stirring bar Pd(OAc)$_2$ (2.8 mg, 0.013 mmol), P$^t$Bu$_2$Me.HBF$_4$ (6.2 mg, 0.025 mmol), pivalic acid (12.3 mg, 0.125 mmol), 1,2,4,5-tetracyanobenzene (22.3 mg, 0.125 mmol), potassium carbonate (54 mg, 0.38 mmol), and bromobenzene (0.275 mmol) were sequentially added under a flow of N$_2$. Anhydrous toluene (0.4 mL) was added and a septum-cap was crimped on the vial to form a seal. The reaction mixture was heated in a 120° C. oil bath for 12 hours. The resulting mixture was cooled to room temperature and filtered through a layer of Celite® (5 mL) using dichloromethane (DCM). The filtrate was concentrated under reduced pressure and the residue was purified by column chromatography on silica gel (eluent: hexanes/DCM) affording the corresponding monoarylated product in 40% yield and the diarylated product in 32% yield.

Example 5

Direct Polycondensation of DCBT with 2,7-dibromo-9,9-dioctylfluorene

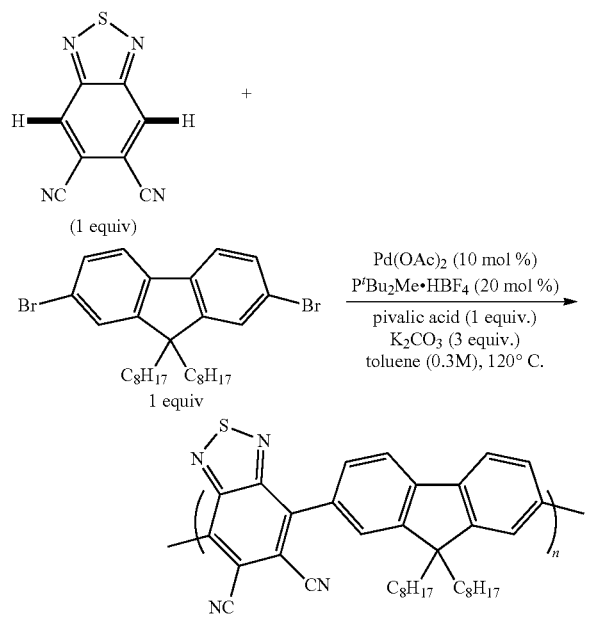

The polycondensation of DCBT with 2,7-dibromo-9,9-dioctylfluorene was carried out in the presence of Pd(OAc)$_2$ (10 mol %), P$^t$Bu$_2$Me.HBF$_4$ (20 mol %), pivalic acid (1 equiv), and K$_2$CO$_3$ (3 equiv) in toluene for 32 hours. Under the reaction conditions, both starting materials were consumed. After concentration, the filtrate of the reaction mixture was passed through Celite® and precipitated from methanol, forming a yellow film solid in 98% yield.

Example 6

2-Octyl-5,6-dicyano-2H-benzo[d][1,2,3]triazole (DCBTz)

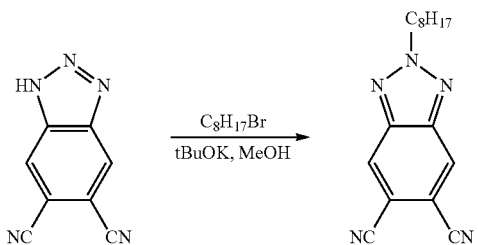

5,6-Dicyano-1H-benzotriazole (169 mg, 1.0 mmol), 1-bromooctane (195 mg, 1.0 mmol), potassium tert-butoxide (113 mg, 1 mmol), and methanol (5 mL) were mixed in a round-bottomed flask equipped with a condenser. The reaction mixture was refluxed overnight. The mixture was cooled down to room temperature and methanol was removed with a rotary evaporator. The resulting mixture was then extracted with CHCl$_3$ and the organic phase was washed with water and dried over Na$_2$SO$_4$. The resulting off-white solid was purified by column chromatography (80 mg, 30%).

Example 7

General Procedure for Pd(II)-catalyzed Direct Diarylation of DCBT, DCBTz, and DCQ To an oven-dried 5 mL collared tube (CEM Corp., Prod #89079-404) containing a stirring bar, Pd(OAc)$_2$ (1.4 mg, 0.006 mmol), P$^t$Bu$_2$Me.HBF$_4$ (3.1 mg, 0.012 mmol), pivalic acid (12.3 mg, 0.125 mmol), DCBT (23.3 mg, 0.125 mmol), potassium carbonate (52 mg, 0.38 mmol), and arylbromide (0.275 mmol unless otherwise noted) were sequentially added under a flow of N$_2$ for the arylation of DCBT derivatives. Anhydrous toluene (0.5 mL) was added and a septum-cap was crimped on the vial to form a seal. The reaction mixture was heated in a 120° C. oil bath for a certain amount of time until the reaction was judged complete by examining aliquots with GC/MS or $^1$H NMR spectroscopy. The resulting mixture was cooled to room temperature and filtered through a layer of Celite® (5 mL) using dichloromethane (DCM). The filtrate was concentrated under reduced pressure and the residue was purified by column chromatography on silica gel (eluent: hexanes/DCM or DCM/ethyl acetate), affording the corresponding diarylated products. The same procedure was used for DCBTz and DCQ derivatives using DCBTz (28.1 mg, 0.125 mmol) or DCQ (29.8 mg, 0.125 mmol) in place of DCBT and using double the catalyst and ligand loading, i.e. 0.012 mmol of Pd(OAc)$_2$ and 0.024 mol of P$^t$Bu$_2$Me.HBF$_4$.

Example 8

Optimization of Diarylation of DCBT

Optimization of catalytic system for the direct diarylation of DCBT with phenyl halides.

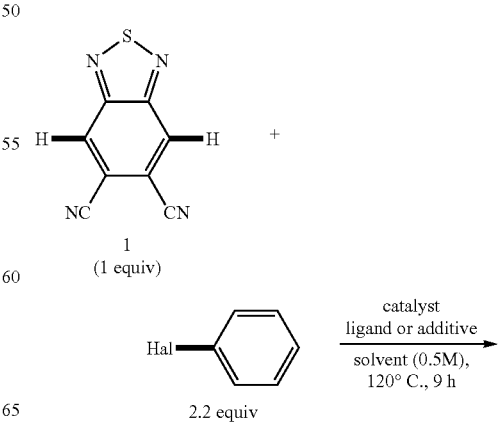

-continued

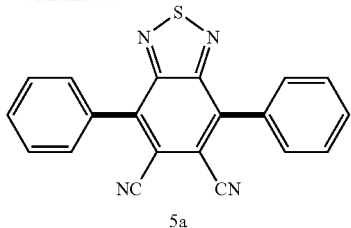

5a 0.006 mmol), P$^t$Bu$_2$Me.HBF$_4$ (6.2 mg, 0.025 mmol), pivalic acid (6.3 mg, 0.063 mmol), DNQx (34.5 mg, 0.125 mmol), anhydrous K$_3$PO$_4$ (58 mg, 0.28 mmol), and arylbromide (0.275 mmol) were sequentially added under a flow of N$_2$. Anhydrous toluene (0.3 mL) was added and a septum-cap was crimped on the vial to form a seal. The reaction mixture was heated in a 120° C. oil bath for certain amount of time until the reaction was judged complete by examining aliquots with GC/MS or $^1$H NMR spectroscopy. The resulting mixture was cooled to room temperature and filtered through a layer of Celite® (5 mL) using dichloromethane (DCM). The filtrate

| Entry | Hal | Catalyst | Ligand | Additives (1 eq) | Base (3 eq) | Solvent | Yield (%)* |
|---|---|---|---|---|---|---|---|
| 1 | I | 10 mol % Pd(OAc)$_2$ | — | Ag$_2$O | — | TFA | 0 |
| 2 | Br | 10 mol % Pd(OAc)$_2$ | 20 mol % P$^t$Bu$_2$Me•HBF$_4$ | pivalic acid | K$_2$CO$_3$ | toluene | 90% |
| 3 | Br | 10 mol % Pd$_2$(dba)$_3$ | 20 mol % P$^t$Bu$_2$Me•HBF$_4$ | pivalic acid | K$_2$CO$_3$ | toluene | 58% |
| 4 | Br | 5 mol % Pd(OAc)$_2$ | 10 mol % P$^t$Bu$_2$Me•HBF$_4$ | pivalic acid | K$_2$CO$_3$ | toluene | 99% |
| 5 | Br | 2 mol % Pd(OAc)$_2$ | 4 mol % P$^t$Bu$_2$Me•HBF$_4$ | pivalic acid | K$_2$CO$_3$ | toluene | 89% |
| 6 | Br | 5 mol % Pd(OAc)$_2$ | 10 mol % P$^t$Bu$_2$Me•HBF$_4$ | — | K$_2$CO$_3$ | toluene | 26% |
| 7 | Br | 5 mol % Pd(OAc)$_2$ | — | pivalic acid | K$_2$CO$_3$ | toluene | trace |

*Isolated yield after purification.
— denotes not used

Example 9

Synthesis of 2,3-diethyl-6,7-dinitroquinoxaline (DNQx)

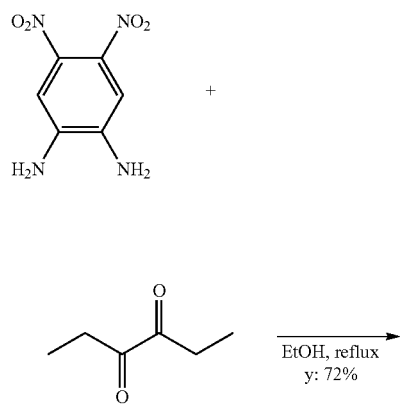

4,5-Dinitro-1,2-phenylenediamine (1000 mg, 5.0 mmol), 3,4-hexadione (685 mg, 6.0 mmol) and ethanol (50 mL) were mixed in a round bottom flask equipped with a condenser. The reaction mixture was refluxed overnight. The mixture was cooled down to room temperature and ethanol was removed under reduced pressure. It was then extracted with methylene chloride and the organic phase was washed with water and dried over Na$_2$SO$_4$. The product obtained as off-white solid (1000 mg, 72%) was purified by column chromatography.

Example 10

Arylation on 2,3-diethyl-6,7-dinitroquinoxaline (DNQx)

To an oven-dried 5 mL collared tube (CEM Corp., Prod #89079-404) containing a stirring bar Pd$_2$(dba)$_3$ (5.7 mg, was concentrated under reduced pressure and the residue was purified by column chromatography on silica gel (eluent: hexanes/DCM or DCM/ethyl acetate), affording the corresponding diarylated products.

Example 11

Optimization of Diarylation of DNQX

Optimization of Reaction Conditions—Screening Catalysts:

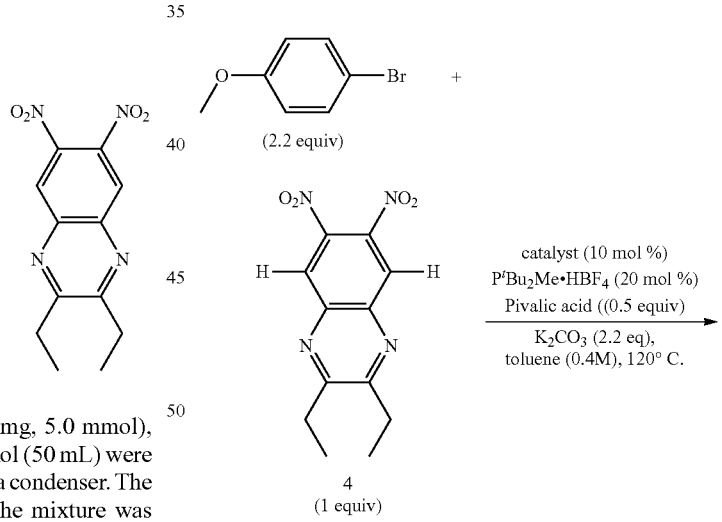

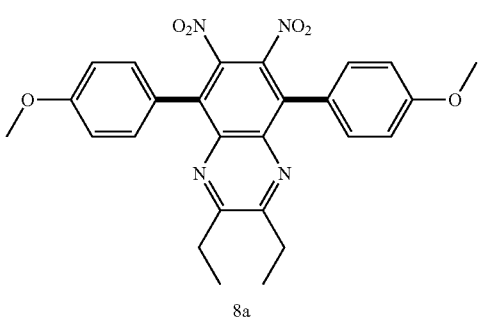

8a

| Entry | Catalyst | Yield (%) |
|---|---|---|
| 1 | Pd(OAc)$_2$ | 52% |
| 2 | (AllylPdCl)$_2$ | 38% |
| 3 | Herrmann | <1% |
| 4 | [(SIPr)PdCl$_2$]$_2$ [444910-17-2] | <1% |
| 5 | Pd$_2$dba$_3$ (5 mol %) | 65% |
| 6 | Pd(PhCN)Cl$_2$ | 46% |

Optimization of Reaction Conditions—Screening Bases:

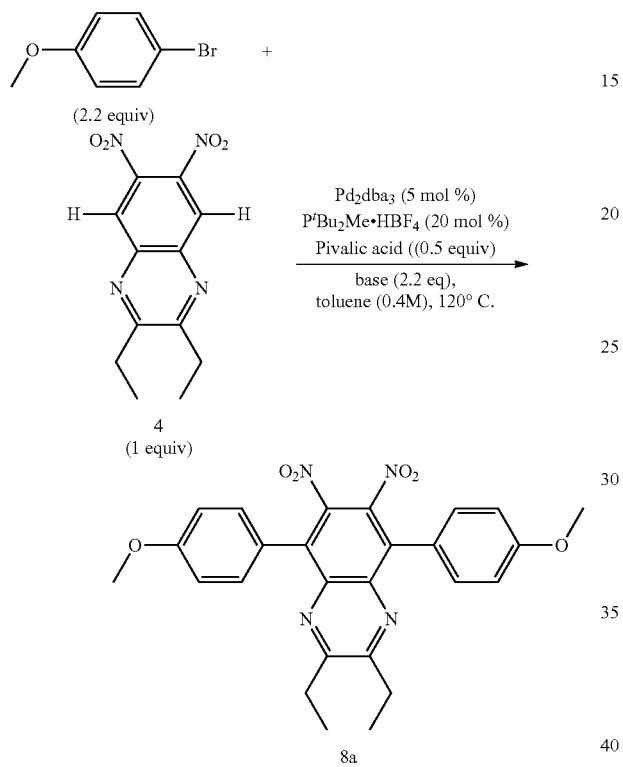

| Entry | Base | Yield (%) |
|---|---|---|
| 1 | Cs$_2$CO$_3$ | <1% |
| 2 | K$_3$PO$_4$ | 72% |
| 3 | KOAc | 40% |
| 4 | K$_2$CO$_3$ | 65% |
| 5 | KHCO$_3$ | 35% |
| 6 | Na$_2$CO$_3$ | No reaction |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method comprising reacting a dicyanobenzodiimine with a first aryl group, in a first C—H activated coupling, wherein the dicyanobenzodiimine comprises the structure:

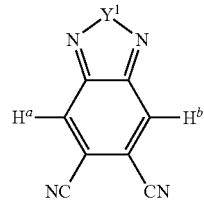

wherein $Y^1$ is selected from the group consisting of O, S, Se, NR$^1$, and C(R$^1$)═C(R$^1$); R$^1$ is independently selected at each occurrence from the group consisting of hydrogen, halogen, a C$_1$-C$_{30}$ alkyl group, a C$_1$-C$_{30}$ heteroalkyl group, a C$_5$-C$_{10}$ heteroaryl group; and wherein a covalent bond is formed between the first aryl group and the dicyanobenzodiimine such that H$^a$ is substituted by the first aryl group;

wherein the first aryl group has at least one labile bond and is selected from the following structures:

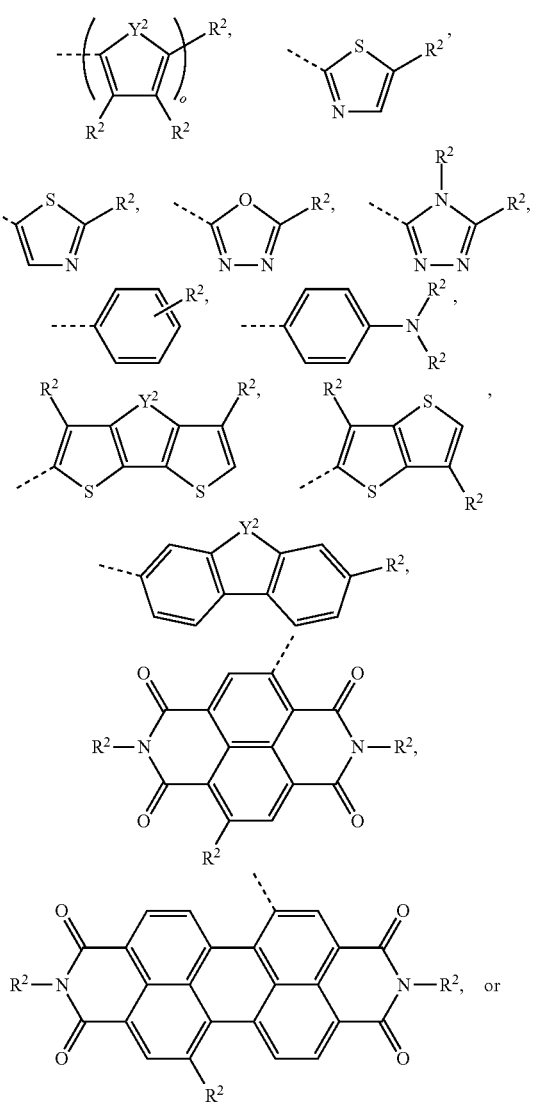

-continued

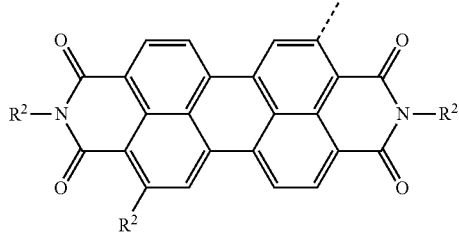

wherein "- - -" denotes the bond which is formed between the first aryl group and the dicyanobenzodiimine; $Y^2$ independently selected at each occurrence from the group consisting of O, S, Se, Ge, $C(R^1)_2$, $Si(R^1)_2$, $Ge(R^1)_2$, and $NR^1$; $R^1$ is independently selected at each occurrence from the group consisting of H, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; $R^2$ is independently selected at each occurrence from the group consisting of hydrogen, halogen, an alkyl group, a heteroalkyl group, a $C_5$-$C_{10}$ aryl group, and a $C_5$-$C_{10}$ heteroaryl group; and o has an integer value from 1-4; and
wherein the reaction occurs in an organic solvent comprising a catalyst, a ligand, and a base.

2. The method of claim 1, wherein the first aryl group is:

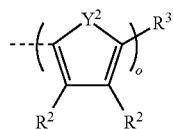

wherein $Y^2$ is sulfur; $R^2$ compromises a heterocyclic ring, and $R^3$ is selected from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; and o has an integer value from 1-3.

3. The method of claim 2, wherein the first aryl group has one of the following structures:

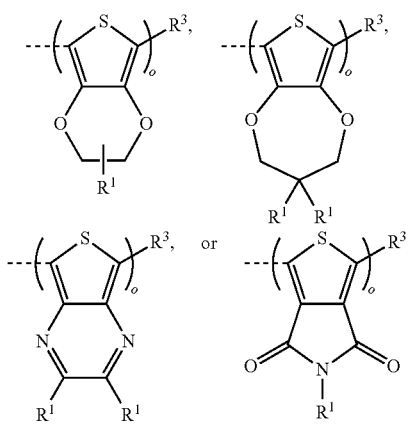

wherein $R^1$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; $R^3$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; and o has an integer value from 1-3.

4. The method of claim 1, wherein the first aryl group is an electron donor and the electron donor is selected from the group consisting of:

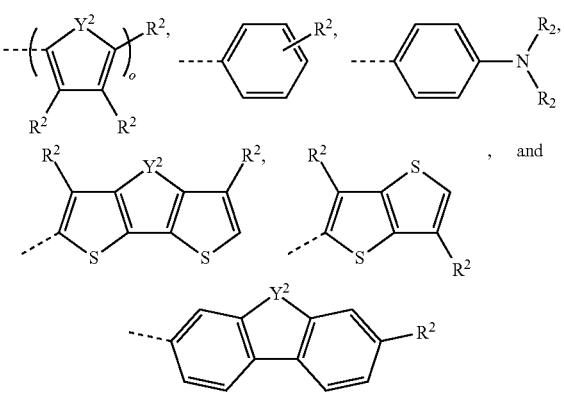

wherein "- - -" denotes the bond formed between the first aryl group and the dicyanobenzodiimine; $Y^2$ is independently at each occurrence from the group consisting of O, S, Se, Ge, $C(R^1)_2$, $Si(R^1)_2$, $Ge(R^1)_2$, and $NR^1$; $R^1$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; $R^2$ independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, or a $C_5$-$C_{10}$ heteroaryl group; and o has an integer value from 1-4.

5. The method of claim 1, wherein the first aryl group is an electron acceptor and the electron acceptor is selected from the group consisting of:

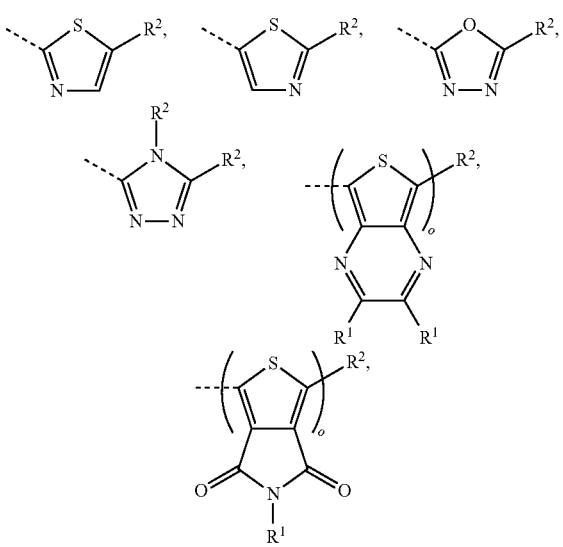

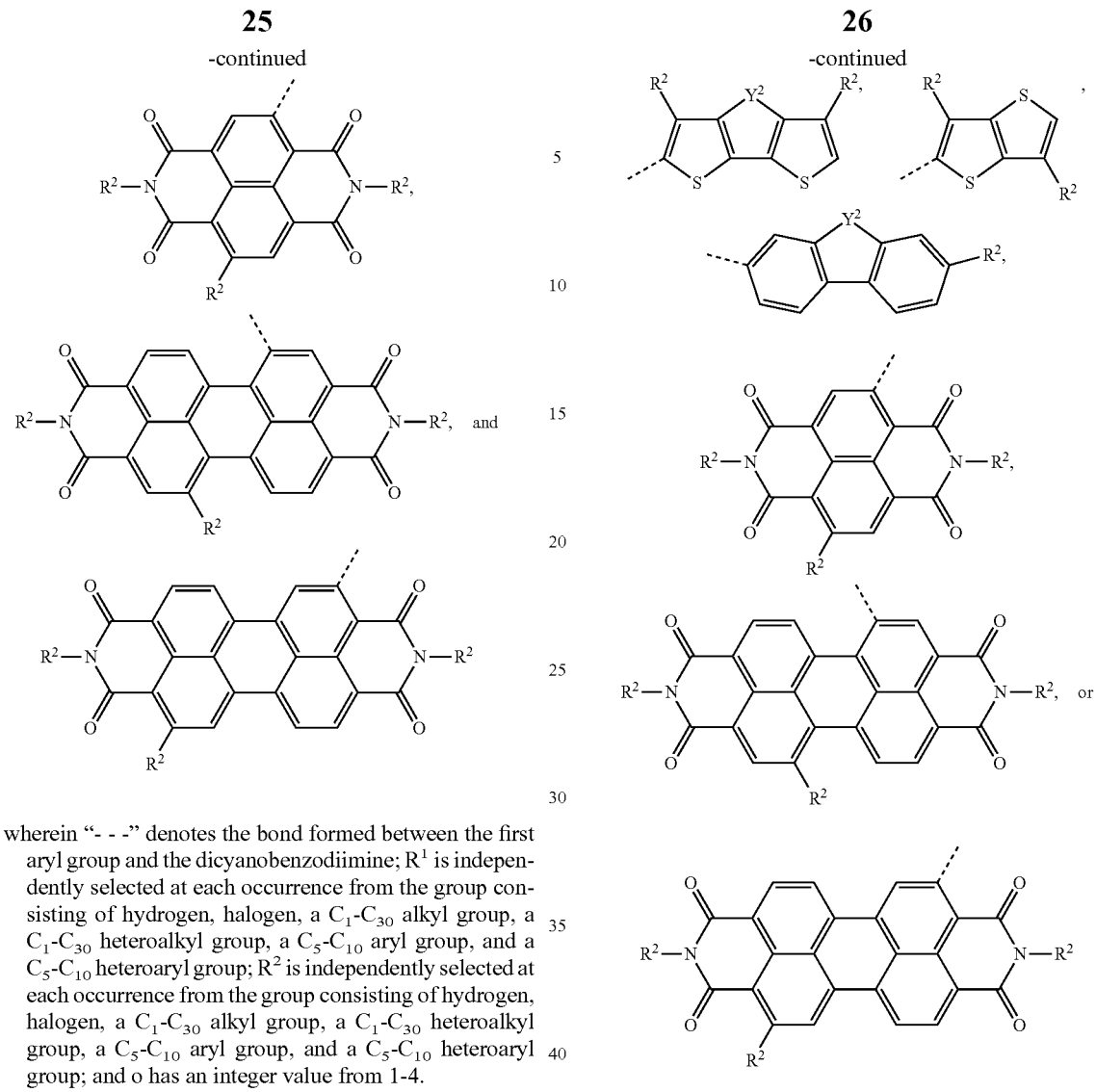

wherein "- - -" denotes the bond formed between the first aryl group and the dicyanobenzodiimine; $R^1$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; $R^2$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; and o has an integer value from 1-4.

6. The method of claim 1, further comprising reacting the dicyanobenzodiimine with a second aryl group in a second C—H activated coupling, whereby a covalent bond is formed between the second aryl group and the dicyanobenzodiimine such that $H^b$ is substituted with the second aryl group;

wherein the second aryl group has at least one labile bond and is selected from the following structures:

wherein "- - -" denotes the bond formed between the second aryl group and the dicyanobenzodiimine; $Y^2$ is independently selected at each occurrence from the group consisting of O, S, Se, Ge, $C(R^1)_2$, $Si(R^1)_2$, $Ge(R^1)_2$, and $NR^1$; $R^1$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; $R^2$ is independently selected at each occurrence from the group consisting of hydrogen, halogen, a $C_1$-$C_{30}$ alkyl group, a $C_1$-$C_{30}$heteroalkyl group, a $C_5$-$C_{10}$ aryl group, and a $C_5$-$C_{10}$ heteroaryl group; and o has an integer value from 1-4.

7. The method of claim 6, wherein the first aryl group and the second aryl group are identical.

8. The method of claim 6, wherein the first aryl group and the second aryl group are different.

9. The method of claim 6, wherein the first aryl group and the second aryl group are independently electron donor groups, wherein the electron donor groups are independently selected from the group consisting of:

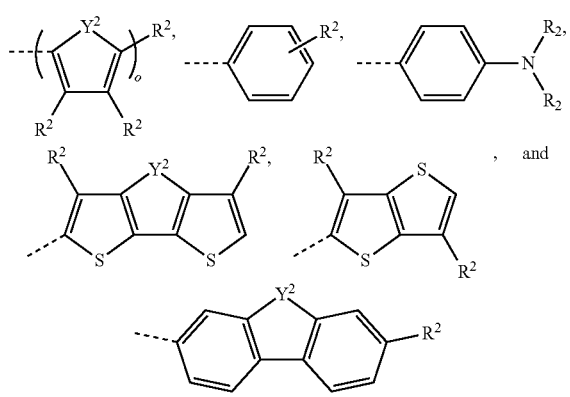

wherein "- - -" denotes the bond formed between the first aryl group and the dicyanobenzodiimine; $Y^2$ is independently selected at each occurrence from the group consisting of O, S, Se, Ge, $C(R^1)_2$, $Si(R^1)_2$, $Ge(R^1)_2$, and $NR^1$; $R^1$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; $R^2$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; and o has an integer value from 1-4.

10. The method of claim 6, wherein the first aryl group and the second aryl group are independently electron acceptor groups, wherein the electron acceptors are selected from the group consisting of:

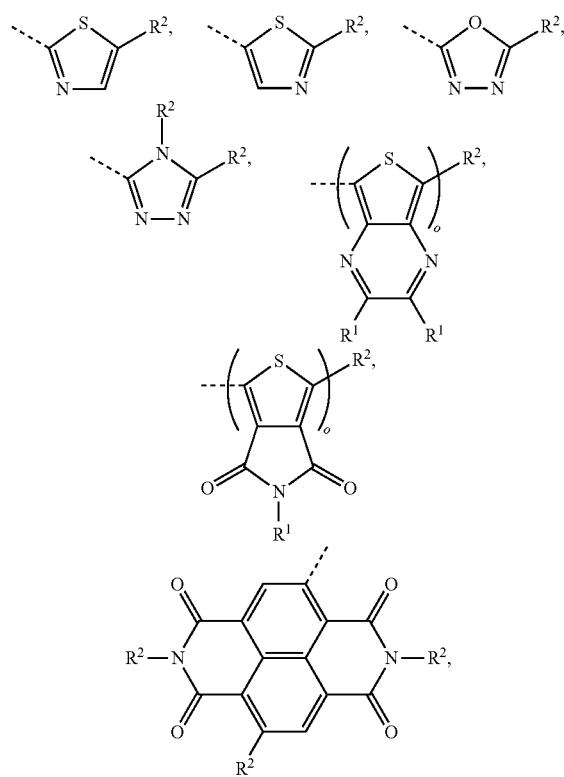

-continued

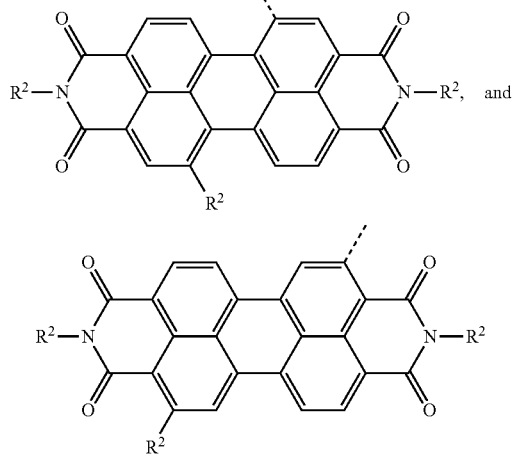

wherein "- - -" denotes the bond formed between the first aryl group and the dicyanobenzodiimine; $Y^2$ is independently selected at each occurrence from the group consisting of O, S, Se, Ge, $C(R^1)_2$, $Si(R^1)_2$, $Ge(R^1)_2$, and $NR^1$; $R^1$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; $R^2$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; and o has an integer value from 1-4.

11. The method of claim 6, wherein the first aryl group is an electron acceptor and the second aryl group is an electron donor or the first aryl group is an electron donor group and the second aryl group is an electron acceptor group;

wherein the electron acceptor is selected from the group consisting of:

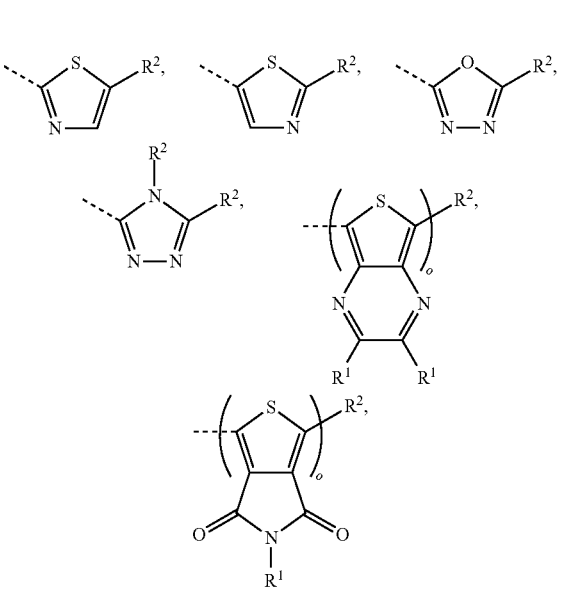

-continued

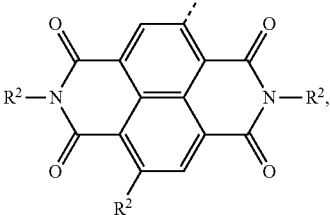

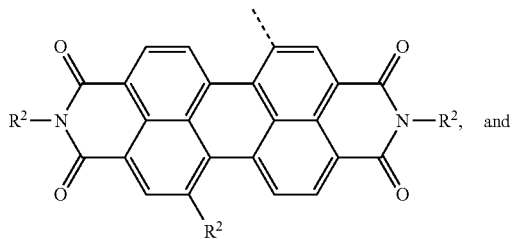, and

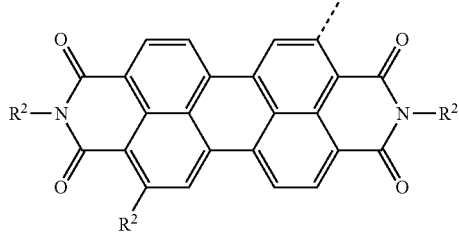

wherein "- - -" denotes the bond formed between the first aryl group and the dicyanobenzodiimine; $Y^2$ is independently selected at each occurrence from the group consisting of O, S, Se, Ge, $C(R^1)_2$, $Si(R^1)_2$, $Ge(R^1)_2$, and $NR^1$; $R^1$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; $R^2$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; and o has an integer value from 1-4; and wherein the electron donor group is selected from the group consisting of:

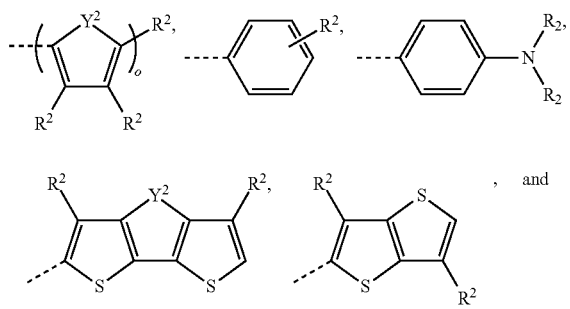

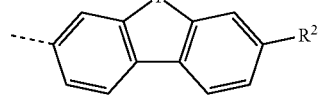

wherein "- - -" denotes the bond formed between the first aryl group and the dicyanobenzodiimine; $Y^2$ is independently selected at each occurrence from the group consisting of O, S, Se, Ge, $C(R^1)_2$, $Si(R^1)_2$, $Ge(R^1)_2$, and $NR^1$; $R^1$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; $R^2$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; and o has an integer value from 1-4.

12. A method comprising reacting a dicyanobenzodiimine with a first aryl group in a first C-H activated coupling, wherein the dicyanobenzodiimine comprises the structure:

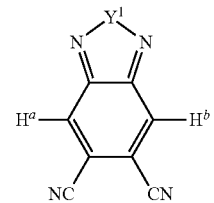

wherein $Y^1$ is selected from the group consisting of O, S, Se, $NR^1$, and $C(R^1)=C(R^1)$; $R^1$ is independently selected at each occurrence from the group consisting of hydrogen, halogen, an alkyl group, a heteroalkyl group, an aryl group, and a heteroaryl group; and wherein a covalent bond is formed between the first aryl group and the dicyanobenzodiimine such that $H^a$ is substituted by the first aryl group; and further reacting the dicyanobenzodiimine with a second aryl group in a second C—H activated coupling, whereby a covalent bond is formed between the second aryl group and the dicyanobenzodiimine such that $H^b$ is substituted with the second aryl group;

wherein the first and second aryl groups each have at least one labile bond and are selected from the following structures:

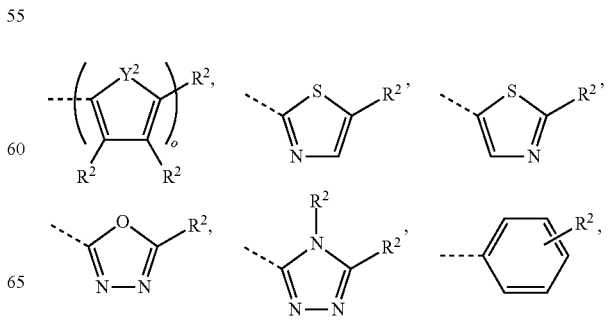

-continued

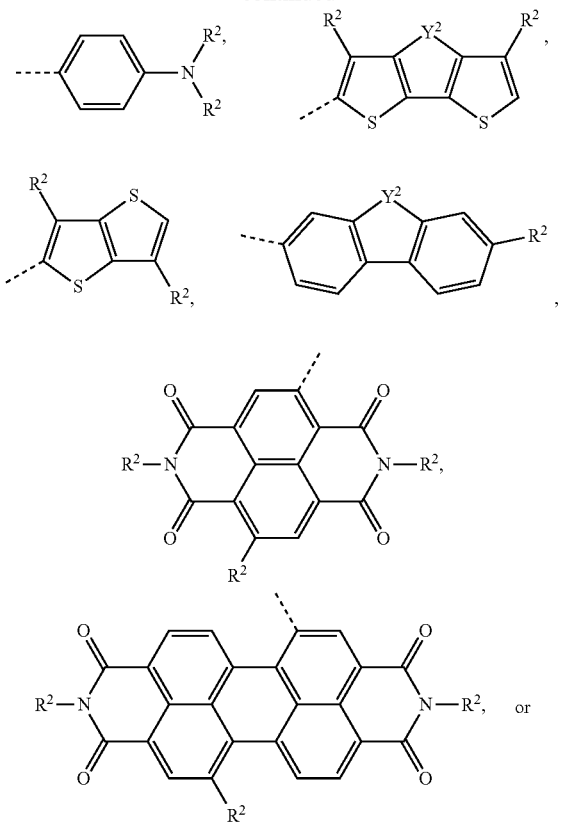

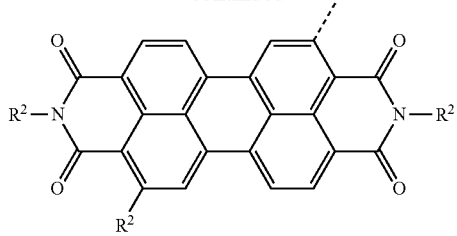

wherein "- - -" denotes the bond which is formed between the first aryl group and the dicyanobenzodiimine; $Y^2$ independently selected at each occurrence from the group consisting of O, S, Se, Ge, $C(R^1)_2$, $Si(R^1)_2$, $Ge(R^1)_2$, and $NR^1$; $R^1$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; $R^2$ is independently selected at each occurrence from the group consisting of hydrogen, halogen, a $C_1$-$C_{30}$ alkyl group, a $C_1$-$C_{30}$ heteroalkyl group, a $C_5$-$C_{10}$ aryl group, and a $C_5$-$C_{10}$ heteroaryl group; and o has an integer value from 1-4; and wherein the reaction occurs in an organic solvent comprising a catalyst, a ligand, and a base.

13. The method of claim 12, wherein the first aryl group and the second aryl group are identical.

14. The method of claim 12, wherein the first aryl group and the second aryl group are different.

* * * * *